US008432279B2

(12) United States Patent
Yao et al.

(10) Patent No.: US 8,432,279 B2
(45) Date of Patent: Apr. 30, 2013

(54) MULTI-STAGE COLOR ACTIVATED SYSTEM TO DETECT UNAUTHORIZED PROCESSING OF MEDICAL DEVICES

(75) Inventors: Min Yao, Vernon Hills, IL (US); Kan P. Lu, Algonquin, IL (US)

(73) Assignee: Medline Industries, Inc., Mundelein, IL (US)

( * ) Notice: Subject to any disclaimer, the term of this patent is extended or adjusted under 35 U.S.C. 154(b) by 435 days.

(21) Appl. No.: 12/821,908

(22) Filed: Jun. 23, 2010

(65) Prior Publication Data

US 2011/0316696 A1 Dec. 29, 2011

(51) Int. Cl.
*G08B 21/00* (2006.01)
(52) U.S. Cl.
USPC .......................................................... 340/540
(58) Field of Classification Search .................. 340/540, 340/539.12, 555; 422/28
See application file for complete search history.

(56) References Cited

U.S. PATENT DOCUMENTS

| | | | |
|---|---|---|---|
| 3,149,992 A | 9/1964 | Lawton | |
| 5,053,339 A | 10/1991 | Patel | |
| 6,544,925 B1 | 4/2003 | Prusik et al. | |
| 6,585,934 B1 * | 7/2003 | Oberleitner et al. | 422/28 |
| 6,752,430 B2 | 6/2004 | Holt et al. | |
| 7,244,252 B2 * | 7/2007 | Berndt | 606/1 |
| 7,682,696 B2 * | 3/2010 | Dean et al. | 428/412 |
| 2002/0012610 A1 * | 1/2002 | Dufresne et al. | 422/28 |
| 2007/0017042 A1 * | 1/2007 | Cincotta et al. | 8/643 |

* cited by examiner

*Primary Examiner* — Phung Nguyen
(74) *Attorney, Agent, or Firm* — David Noskowicz; Philip H. Burrus, IV (57) ABSTRACT

A medical device (101), such as a blood pressure cuff or other device, includes an unauthorized reprocessing warning (406) printed in a first printable media (103). The first printable media (103) is configured to change from a first state to a second state upon exposure to an applied stimulus (203). A mask (407) is printed on or about the unauthorized reprocessing warning (406) in a second printable media (106). The second printable media (106) is configured to also change state upon exposure to an applied stimulus (203). The unauthorized reprocessing warning (406) is legible only after exposure to the applied stimulus (203). However, application of a reversion stimulus 306 will render the unauthorized reprocessing warning (406) non-legible.

19 Claims, 5 Drawing Sheets

MULTI-STAGE COLOR ACTIVATED SYSTEM TO DETECT UNAUTHORIZED PROCESSING OF MEDICAL DEVICES

BACKGROUND

1. Technical Field

This invention relates generally to detection systems for processing of medical devices, and more particularly to a multi-stage color activated system that changes color during processing events to provide a warning when unauthorized processing occurs.

2. Background Art

Many medical devices are "single-use" devices. For example, when a surgeon uses a scalpel, it is used only for one procedure on one patient. To ensure sterility, it is not washed and used again. Instead, a surgeon will use a new scalpel when performing another procedure. One-time-use devices tend to be disposable devices, such as syringes, needles, scalpels, containers and the like.

Some other medical devices can be reprocessed and reused. Illustrating by way of example, a blood pressure cuff can be used on multiple patients. However, to ensure that germs, diseases, and microbes are not transmitted between patients, proper processing is frequently required between uses. The processing can include, for example, washing the device and exposing it to high heat to kill any microbes or germs on the device.

While many reputable service providers offer medical device reprocessing, some others employ reprocessing methods that do not meet the device manufacturer's requirements. Using the example from the preceding paragraph, a manufacturer may require that a blood pressure cuff be both washed and exposed to high heat prior to reuse. However, after reprocessing there is generally no easy way to determine whether the manufacturer's reprocessing techniques have been followed. There is thus a need for a method to determine whether a medical device has been properly reprocessed.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing FIG. 1 would refer to an element, 10, shown in figure other than FIG. 1.

A problem exists where reprocessing services providers attempt to process medical devices without complying with the proper procedures. This can be especially troublesome when the product is under a manufacturer's warranty and a manufacturer employs specific reprocessing procedures to ensure quality. If such a device should fail, it can be difficult to tell whether the failure was due to design or improper reprocessing. It would be advantageous for the manufacturer, distributor or supplier to be able to determine whether or how the device has been reprocessed.

In the world of medical device reprocessing, the reprocessing steps generally involve cleaning and sterilizing the device. A clean device looks clean, whether it has been reprocessed properly or not. However, an improperly reprocessed device can still carry germs, disease, or microorganisms. Embodiments of the present invention provide a solution that is allows an end user to quickly and easily determine whether the device has been properly reprocessed.

Embodiments of the present invention provide a medical device having a logo or print label that serves as an unauthorized reprocessing warning. The warning is configured as a multi-stage color activation system. A medical device, such as a blood pressure cuff, pulse oximeter probe, or other device has comprising an unauthorized reprocessing warning printed thereon. The unauthorized reprocessing warning is printed in a first printable media. The first printed media is configured to change from a first state to a second state upon exposure to an applied stimulant such as moisture or heat. Illustrating by way of example, the first state could be a transparent or pellucid state, while the second state is a predetermined color, such as black.

A mask is then printed along the same area as the unauthorized reprocessing warning. In one embodiment, the mask has a perimeter that surrounds the unauthorized reprocessing warning. The mask can be printed beneath or atop the unauthorized reprocessing warning. In one embodiment, the mask is printed in a second printable media. The second printable media is configured to change from the same first state as that of the first printable media to a second state upon exposure to the applied stimulant. In one embodiment, the second states of the first printable media and the second printable media are different colors, such that the unauthorized reprocessing warning becomes visible and legible against the mask after exposure to the stimulant.

Illustrating operation by way of example, presume that the first state of both the first printable media and the second printable media are transparent. Now presume that the second state of the first printable media is black, and the second state of the second printable media is yellow. When the first printable media and second printable media are applied, neither the warning label nor the mask is visible. However, if the medical device is exposed to the stimulant, which may be, for example, moisture or heat encountered during unauthorized reprocessing, both the first printable media and the second printable media change to the second state. Consequently, a black warning label appears against a yellow shield. The first printable media can be configured as text, and may present a warning message such as "Warning! Unauthorized reprocessing has occurred."

To permit authorized reprocessing, in one embodiment both the first printable media and the second printable media can be returned to the first state through the application of a second stimulus. Examples of the second stimulus include application of heat beyond temperature thresholds encountered in normal reprocessing systems, or exposure to ultraviolet or other radiation. Thus, when an authorized reprocessor processes the medical device, the second stimulus can be applied as a final step, thereby rendering the unauthorized reprocessing warning non-visible again.

Embodiments of the present invention offer numerous advantages over prior art sanitization detection systems. For example, prior art systems employing color activation employ a label or printing that includes only a one-stage activation system. Consequently, when exposed to a stimulus, an irreversible color change occurs. Consequently, these devices cannot be reprocessed.

Embodiments of the present invention permit authorized reprocessing through the use of the multi-stage color activation system. When the second stimulus is applied, the warning message can be configured to disappear. Accordingly, a user can be confident that the device has been reprocessed in accordance with the manufacturer's requirements.

Next, embodiments of the present invention appear—before use and after authorized reprocessing—just like ordinary medical devices. No special mechanical or geometric additions or reconfigurations are required. However, one the media is activated, a clear, easily visible message will appear alerting the end user that reprocessing has occurred. Further, additional messages can be included alerting the end user to other information, such as the fact that the medical device may no longer be under warranty.

Figure 1:
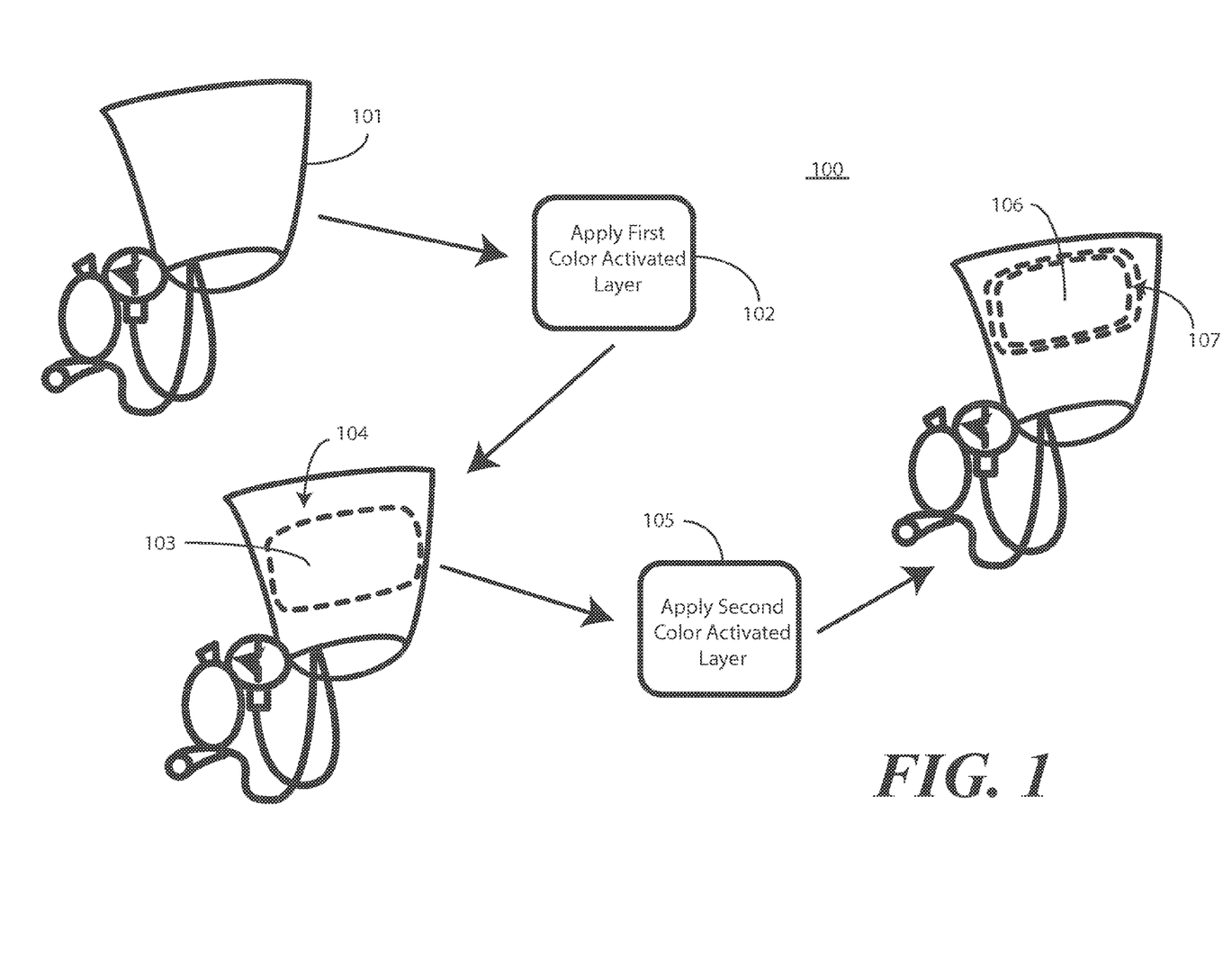
FIG. 1 illustrates a method of manufacturing a medical device in accordance with embodiments of the invention.

Turning now to FIG. 1, illustrated therein is one method 100 of manufacturing a medical device with a multi-stage color activation system in accordance with embodiments of the invention. For illustrative purposes, a blood pressure cuff will be used herein as an illustrative embodiment of a medical device. However, it will be obvious to those of ordinary skill in the art that the method 100 could be used with any number of medical devices. Examples of such medical devices include sequential compression devices, impads, foot cuffs, pulse oximeter probes, pressure infusors, cervical collars, pneumatic tourniquets, fetal belts, splints, roll belts, masks, and so forth. Additional devices include gas or oxygen masks, tracheal tube stylets, breathing circuits, medicinal nebulizers, surgical blades, ear, nose, or throat burs, surgical drills, forceps, retractors, dislodgers, suturing devices, surgical chisels, surgical cutting devices, surgical snares, surgical staplers, needle guides, surgical dissectors, biopsy brushes, surgical motors, laser instruments, scissors, arthroscopes, traction apparatuses, reamers, rasps, knives, osteomes, taps, staple drivers, surgical cables, bands, or belts, trocars, tourniquets, infusors, stethoscopes, endoscopic instruments, injectors, oximeters, catheters, laparoscopes, clamps, clips, and so forth. Still more devices can be found in Volume 8, No. 83 of the Federal Register as published Apr. 30, 2003, which is incorporated herein by reference. This list is not inclusive, as other devices can be used as well.

The medical device 101 is initially in its original state, having been structurally manufactured, but not yet having had the printable media disposed thereon. At step 102, a first printable media 103 is applied along at least a portion 104 of the medical device 101. The first printable media 103 can be applied along the portion 104 with the assistance of any number of industrial printing machines, such as roll printers, thermal transfer printers, hot-stamp printers, spray printers, screen printers, and so forth. Note that the portion 104 can be a sub region of the medical device 101, or alternatively can cover substantially all of the medical device 101.

Figure 6:
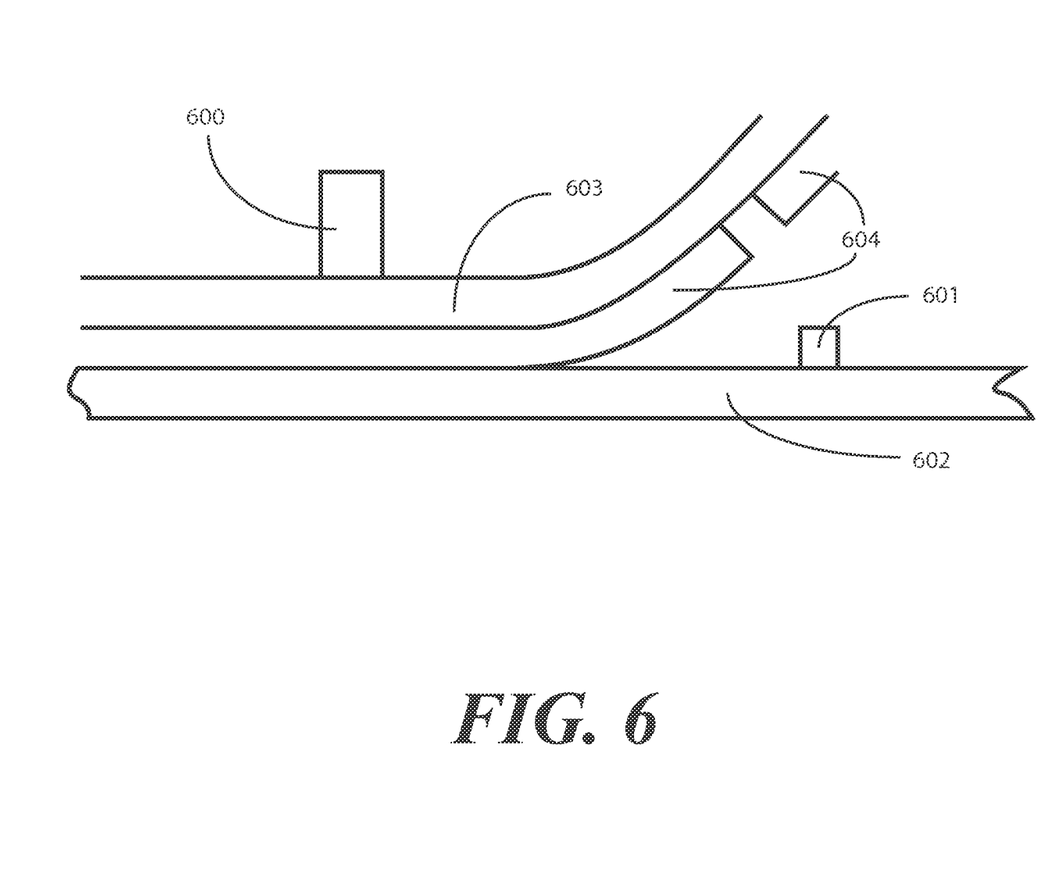
FIG. 6 illustrates a printing process suitable for use with embodiments of the invention.

Illustrating by example, one suitable printing process is shown in FIG. 6. Turning briefly to FIG. 6, illustrated therein one example of a thermal transfer printing step as carried out by a thermal transfer printing machine. Thermal transfer printing can be employed on a variety of materials, such as coated metal surfaces, plastics film and other coated materials.

A "pre-coating" process is similar to application of a primer, and provides an "ink-friendly" surface on the material. The color and pattern of thermal transfer printing process can be precisely controlled. A thermal transfer printer with different thermal transfer ribbons is capable to print on medical devices in multi-stage colors.

In the thermal transfer process, the printer head element 600 generates heat. The printer head can be configured with many elements, each of which prints a pixel 601 or dot on the material 602. Heat is transmitted through the polyester backing 603 of the ribbon, thereby causing the resin 604 or "ink" on the ribbon to melt. When the resin 604 melts, it comes into contact with the substrate 602 to form the characters.

Turning now back to FIG. 1, it will be appreciated that embodiments of the method 100 can be implemented in a manufacturing environment by way of an automated process, with one or more printing, conveyance, sorting, diagnostic, or other machines performing the various steps. The machines may be integrated in a network, or may be separately controlled during the various steps. The machines may be responsive to one or more control systems or conventional processors executing unique stored program instructions that control the one or more processors to implement, in conjunction with certain non-processor circuits, some, most, or all of the functions of the applying, reprocessing, receiving, and other steps of the various methods described herein. As such, these functions may be interpreted as steps of a method to perform the applying, reprocessing, or receiving. Alternatively, the various machines or method steps may be responsive to a state machine that has no stored program instructions, or in one or more application specific integrated circuits (ASICs), in which each function or some combinations of certain of the functions are implemented as custom logic. Of course, a combination of the two approaches could be used. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ASICs with minimal experimentation.

The first printable media 103 applied at step 102 is a "color activated" media in that it is configured to transition from a first state having a first color or other visual appearance to a second state having a second color or other visual appearance upon exposure to an applied stimulus. For example, in the first state, after application, the first printable media 103 may be a first color, such as white, yet may transition to a second color, such as yellow, upon exposure to the stimulus. Alternatively, the first printable media 103 may have a first visual appearance, such as being pellucid or transparent prior to exposure to the stimulus, but may change to another color, such as black, after exposure to the stimulus.

Suitable color activated materials performing in accordance with the description above are known in the art. For example, such materials are manufactured by companies like TMC Hallcrest are capable of activation described herein. Their ChromaZone.sup.™ line of products come in many forms, including dispersion form that can be dissolved in ink, powder form, pigmented form for inclusion in thermoplastics, and in thermachromic inks.

At step 105, a second printable media 106 is applied along a second portion 107 of the medical device. In one embodiment, the second portion 107 and the first portion 104 overlap by at least some predetermined amount. In another embodiment, the first portion 104 and the second portion 107 can be the same. In other embodiments, the first portion 104 is a sub-portion of the second portion 107, or vice versa.

The second printable media 106 is also a color activated material in that it is also configured to transition from a first state to a second state upon application of a stimulus. As with the first printable media 103, the second printable media is configured to change from a first color or other visual appearance to a second color or other visual appearance upon exposure to the stimulus.

In one embodiment, the first state of the first printable media 103 and the first state of the second printable media 106 are the same. For example, the first state of the first printable media 103 and the second printable media 106 can both be pellucid. Alternatively, the first state of the first printable media 103 and the second printable media 106 can be a common color, such as white.

In one embodiment, the second states of the first printable media 103 and the second printable media 106 are configured to be different colors or visual appearances. Illustrating by example, after exposure to the stimulus, the first printable media 103 may become yellow in color while the second printable media 106 becomes black. Accordingly, after application of the stimulus, one of the first printable media 103 or the second printable media 106 becomes visible against the other.

Examples of stimuli that can activate the color of the first printable media 103 and second printable media 106 include one or more of heat, chemicals, cleansing agents, sanitization agents, moisture, light, radiation, or combinations thereof. These stimuli are generally present during reprocessing activities. When the medical device 101 is reprocessed, it will frequently be exposed to one or more of these stimuli. Accordingly, in one embodiment, the first printable media 103 and second printable media 106 are configured to both become color activated during a reprocessing process.

The first printable media 103 and second printable media 106 can be configured in different ways. As one non-limiting example, one of the first printable media 103 and second printable media 106 can be configured as text, while the other is configured as a mask. Where the text is configured as an unauthorized reprocessing warning and the mask has a perimeter surrounding this warning, prior to the exposure to the stimulus, the text is initially non-visible and non-legible because the first printable media 103 and second printable media 106 have the same color or visual appearance. However, after exposure to the stimulus, the unauthorized reprocessing warning becomes visible against the mask because the second states of the first printable media 103 and second printable media 106 have different colors and different visual appearances. This will be described in more detail with reference to FIGS. 4 and 5.

Figure 2:
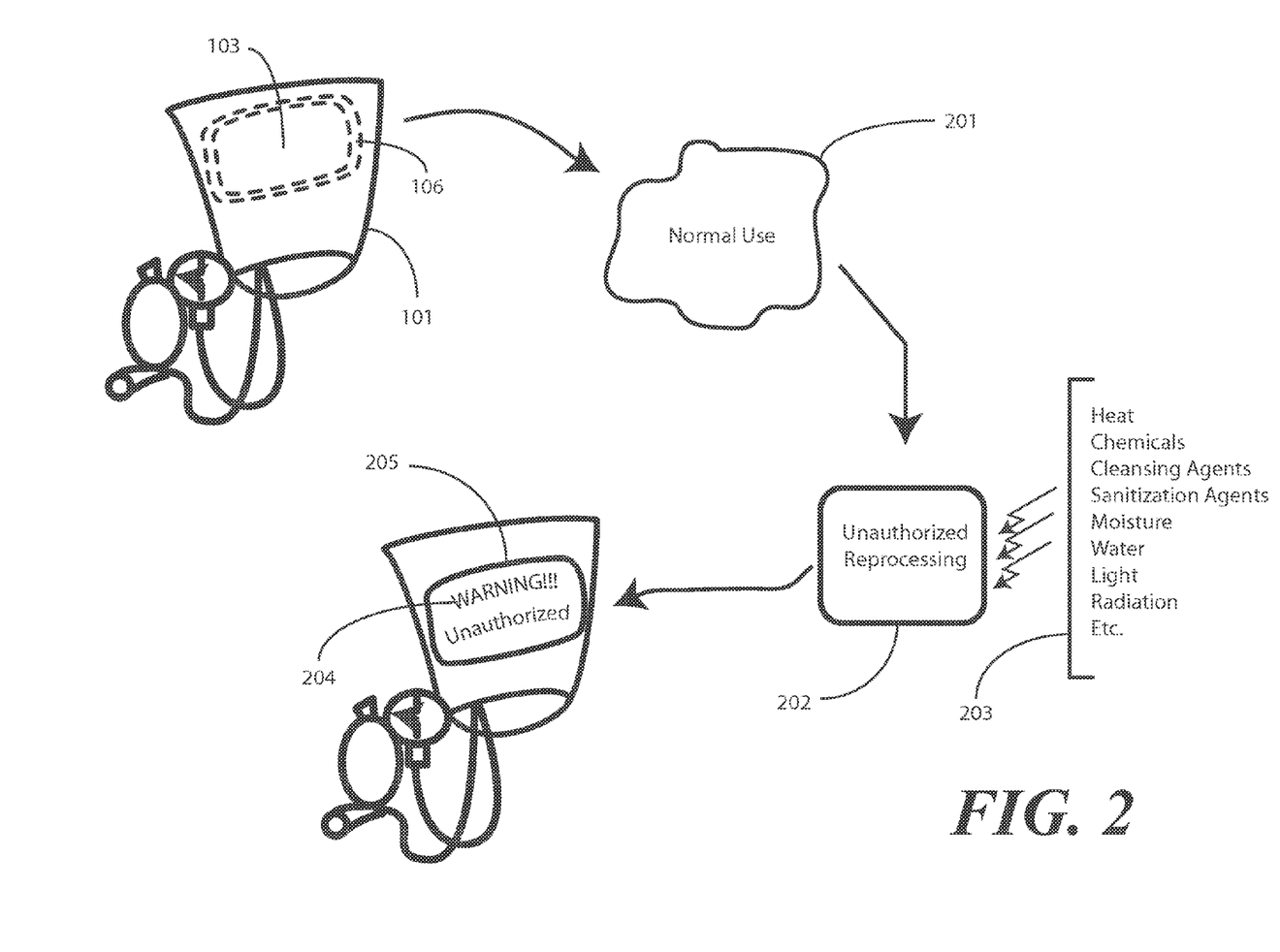
FIG. 2 illustrates a flow diagram of one embodiment of the invention undergoing unauthorized reprocessing and the results that follow.

Turning now to FIG. 2, illustrated therein is a flow chart of how the medical device 101 is used, and how the first printable media 103 and second printable media 106 can be used to alert an end user that unauthorized reprocessing has occurred. More specifically, FIG. 2 illustrates how the first printable media 103 and second printable media 106 reveal the unauthorized reprocessing warning.

The medical device 101 is delivered to the medical services provider or other user without having been exposed to the color activation stimulus. Accordingly, the first printable media 103 and second printable media 106 are in the first state, which can be a pellucid state, a state of common color, or another state where the first printable media 103 is not visible against the second printable media 106 or vice versa.

At step 201, a medical services provider or other end user uses the medical device 101. Once the medical device 101 has been used, the medical device 101 is sent to reprocessing.

At step 202, the medical device 101 is reprocessed. As noted above, this reprocessing step 202 can include exposure to one or more stimuli, including heat, chemicals, cleansing agents, sanitization agents, moisture, light, radiation, or combinations thereof as the medical device 101 is cleaned and sterilized. When this occurs, both the first printable media 103 and second printable media 106 are configured to change to their second states. Where one is configured as an unauthorized reprocessing warning 204 and the other is configured as a mask 205, the former becomes visible and legible against the latter due to their different colors or visual appearances in the second state.

Figure 3:
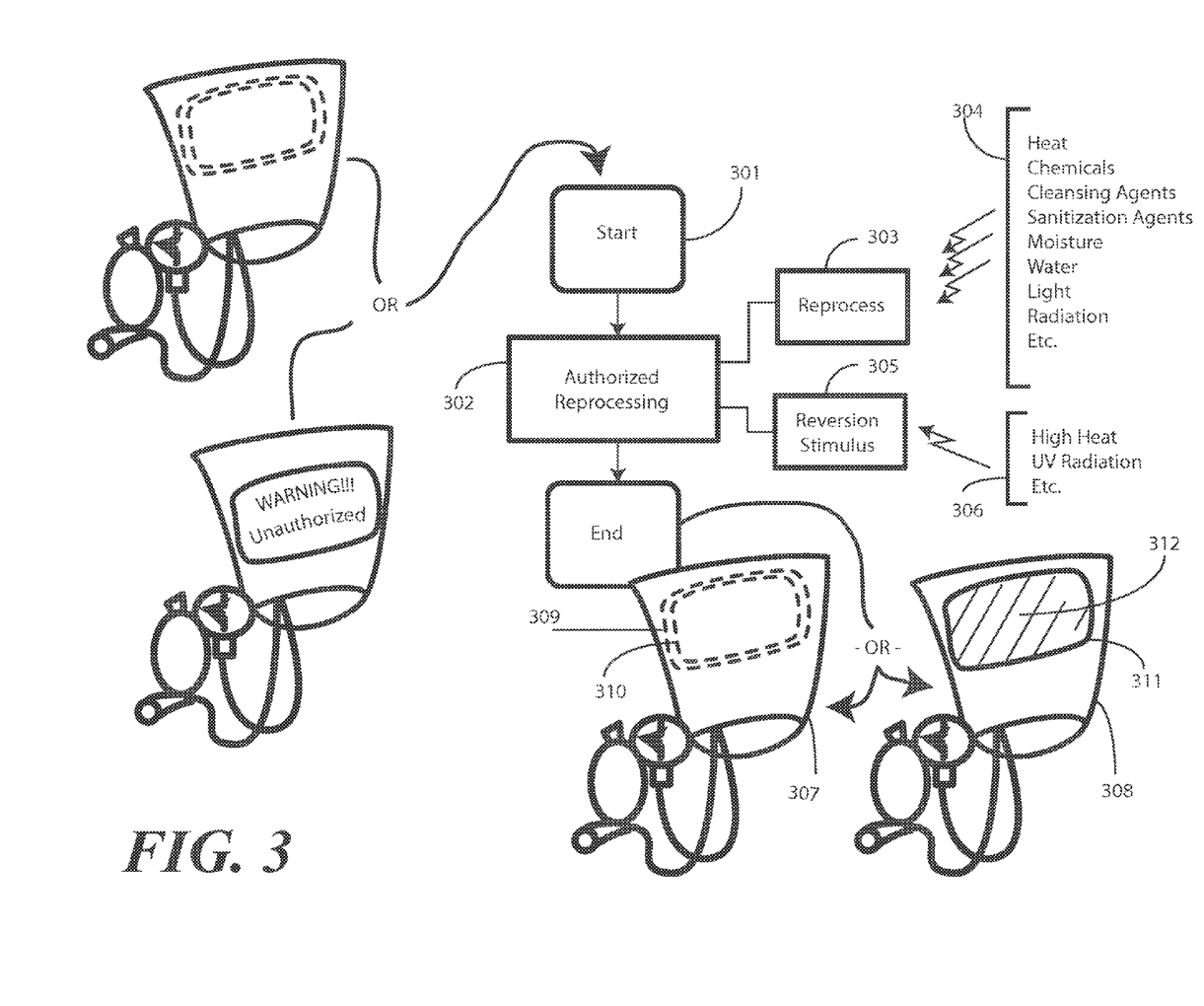
FIG. 3 illustrates a flow diagram of one embodiment of the invention undergoing authorized reprocessing in accordance with embodiments of the invention, as well as the results that follow.

Turning now to FIG. 3, illustrated therein is an alternate method 300 of reprocessing. The method 300 of FIG. 3 is one that may be performed by an authorized reprocessor and includes additional steps beyond that shown in FIG. 2.

At step 301, the used medical device is received. In one embodiment, the used medical device will be received from an end user after unauthorized reprocessing has occurred. Accordingly, the unauthorized reprocessing warning will be visible and legible against the mask. In another embodiment, the used medical device will be received after use and without exposure to a color activating stimulus. In such an embodiment, the unauthorized reprocessing warning will not be visible.

At step 303, the authorized reprocessor will process the used medical device. As noted above, the processing will expose the first printable media and second printable media to one of the processing stimuli 304, and will therefore make the unauthorized reprocessing warning visible. To remove this, at step 305 the processed medical device is exposed to a reversion stimulus 306. Examples of reversion stimuli include one or more of applying heat beyond a predetermined temperature threshold, i.e., heat beyond a temperature typically used in reprocessing, or exposing the medical device to ultraviolet radiation. Other reversion stimuli will be obvious to those of ordinary skill in the art having the benefit of this disclosure.

In one embodiment, both the first printable media and the second printable media are configured to transition to a third state upon application of the reversion stimulus 306. The third state is a color or visual appearance that is different from the second. In one embodiment, the third state can be the same as the first state. For example, if both the first printable media and second printable media have a common color in the first state, they may return to that color in the third state. Alternatively the first state and the third state may be different. For example, both the first printable media and second printable media may be white in the first state, but may turn blue in the second state.

In one embodiment the third state of the first printable media and the second printable media has the same color or visual appearance. Accordingly, when the reversion stimulus 306 is applied, the unauthorized reprocessing warning is no longer visible or legible against the mask due to the common visual appearance.

In another embodiment, one of the first printable media or second printable media has a color substantially darker than the other in the third state. Accordingly, when the reversion stimulus 306 is applied, the darker of the two "blocks out" the other, thereby rendering the lighter color non-visible or non-legible.

Figure 4:
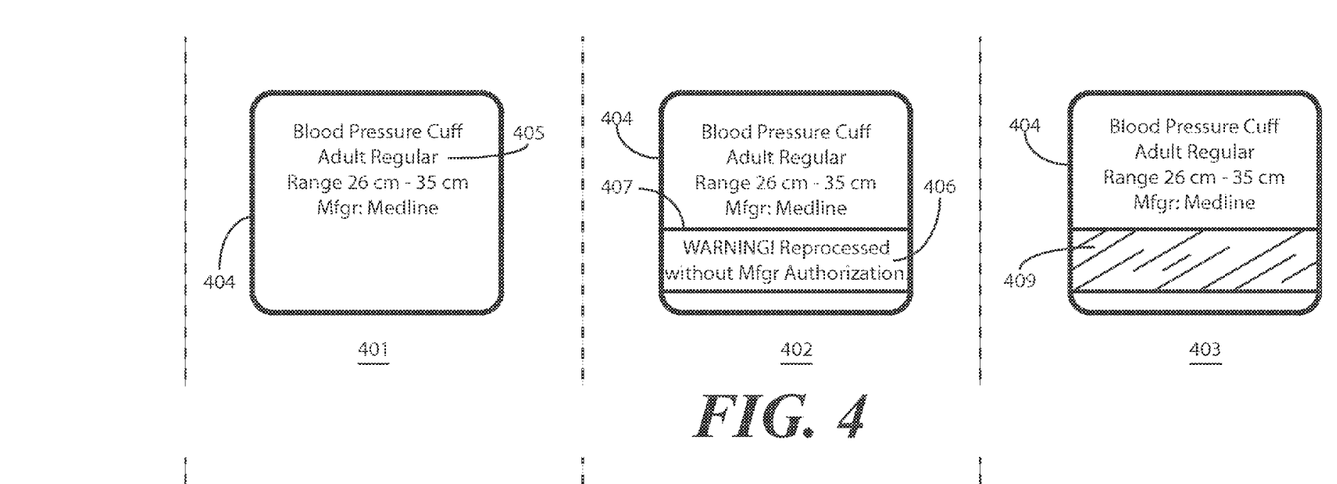
FIG. 4 illustrates one example of a multi-stage color reprocessing identification system in accordance with one embodiment of the invention.
Figure 5:
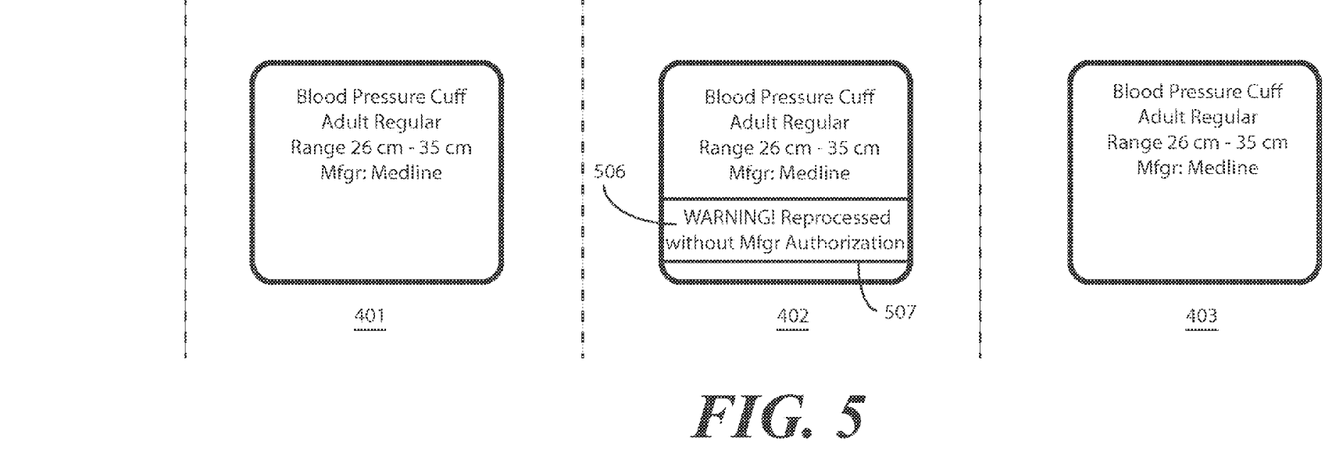
FIG. 5 illustrates another example of a multi-stage color reprocessing identification system in accordance with one embodiment of the invention.

While this will be shown in more detail with reference to FIGS. 4 and 5, it is illustratively shown in FIG. 3 as well. Medical device 307 has a first printable media 309 and second printable media 310 that are pellucid in the third state, i.e., that are pellucid after application of the reversion stimulus 306 at step 305. Accordingly, neither the unauthorized reprocessing warning nor the mask is visible. This will be shown in more detail with respect to FIG. 4.

Medical device 308 has a first printable media 311 and second printable media 312 that are configured to change to a common color in the third state. For example, both the first printable media 311 and second printable media 312 may be configured to change to blue. Accordingly, the first printable media 311 and second printable media 312 are not visible against one another, and appear as a blue shield. This will be shown in more detail with respect to FIG. 5.

Turning now to FIG. 4, illustrated therein is a stage diagram depicting three stages 401,402,403 of a medical device. The first stage 401 is where the medical device has been used but not reprocessed. The second stage 402 is where the medical device has been reprocessed. This stage 402 would be the terminal stage with an unauthorized reprocessor, as unauthorized reprocessors do not complete the third stage 403. The second stage 402 is an intermediate step for an authorized reprocessors, as all authorized reprocessors complete the third stage 403, which is application of the reversion stimulus.

A portion 404 of the medical device is shown in each stage 401,402,403. At stage 401, the portion 404 shows only standard printed information 405. This can include a device identifier, a manufacturer identifier, instructions for use, and the like. The first printable media and the second printable media are in the first state, which in this illustrative embodiment is pellucid. As such, neither the first printable media nor second printable media is visible at this stage 401.

At stage 402, the device has been reprocessed, thereby exposing the device to a color activating stimulus. Accordingly, the first printable media and second printable media transition to their second state. Each second state in this embodiment has a different color. The first printable media is configured here as an unauthorized reprocessing warning 406, and has become visible against the second printable media, which is configured here as a mask 407.

At stage 403, an authorized reprocessor has applied the reversion stimulus, thereby causing the first printable media and the second printable media to transition to a third state. In this illustrative example, the third state is different from the first state. In the third state, both the first printable media and second printable media have the same color, while in the first state, both were pellucid. As the first printable media and the second printable media have the same color, the unauthorized reprocessing warning 406 is no longer visible against the mask 407. Instead, both appear as a common shield 409.

Recall from the discussion above that in one embodiment, one of the first printable media or the second printable media can be configured to be substantially darker after application of the reversion stimulus. Where this is the case, the appearance will be the same as that shown in stage 403 of FIG. 4. The unauthorized reprocessing warning 406 has been "blocked out" by the mask 407, resulting in the appearance of the shield 409. This configuration can be advantageous because some devices are designed to be reprocessed no more than one time. With this configuration, the reprocessor instantly knows whether a reprocessing has occurred when the shield 409 is present.

Turning now to FIG. 5, illustrated therein are the three stages 401,402,403 shown in FIG. 4. The difference between FIGS. 4 and 5 is that the first state and third state of the first printable media and the second printable media are the same. The state is a common color of white.

Thus, while the unauthorized reprocessing warning 506 and mask 507 are visible in stage 402, neither is visible in either stage 401 or 403. Each appears white against a white background. As such, neither is visible or legible.

As described above, a portion or all the surface of a medical product is printed with two media, which can be stimulus sensitive dyes or inks. The media respond to stimuli used in reprocessing tasks, such as heat, moisture, light, or radiation. Upon exposure to one or more of these, the media can be configured to change visual appearance or color.

When the media are first applied, both media can be configured to be colorless or pellucid, or may have a common color. The two media can be printed directly on each other. Alternatively, one media can be printed to "fill" the background of the other along the medical device.

Upon reprocessing, one media becomes visible against the other. Where one media is configured as text, e.g., as an unauthorized reprocessing warning, this text will become visible. Upon application of a reversion stimulus, applied only by authorized reprocessors, the unauthorized reprocessing warning will no longer be visible. This can occur when the media become the same color or when one media "blocks out" the other.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A method of manufacturing a medical device, comprising:
    applying a first printable media along at least a portion of the medical device, the first printable media being configured to transition from a first color to a second color upon exposure to an applied stimulant; and
    applying a second printable media along the at least the portion of the medical device, the second printable media being configured to transition from the first color to a third color upon the exposure to the applied stimulant;

wherein the second color and the third color are different; and after exposure to the applied stimulant the first printable media is configured to change its visual appearance upon exposure to a first reversion stimulant.

2. The method of claim 1, wherein the applied stimulant comprises one or more of heat, chemicals, cleansing agents, sanitization agents, moisture, light, radiation, or combinations thereof.

3. The method of claim 1, wherein after the exposure to the applied stimulant, the second printable media is also configured to change its visual appearance upon exposure to a second reversion stimulant.

4. The method of claim 3, wherein the first reversion stimulant and the second reversion stimulant are different.

5. The method of claim 4, wherein one or more of the first reversion stimulant or the second reversion stimulant comprises one or more of heat beyond a predetermined temperature threshold or ultraviolet radiation.

6. The method of claim 1, wherein the applying the first printable media comprises applying the first printable media as a pattern including one or more of text or a logo.

7. The method of claim 6, wherein the applying the second printable media comprises printing so as to render the pattern non-visible.

8. The method of claim 7, wherein the pattern comprises a warning message that unauthorized reprocessing of the medical device has occurred.

9. The method of claim 1, wherein the first color is non-visible along the at least a portion.

10. A medical device, comprising:
an unauthorized reprocessing warning printed in a first printable media configured to change from a first state to a second state upon exposure to an applied stimulant; and
a mask having a perimeter surrounding the unauthorized reprocessing warning, the mask being printed in a second printable media configured to change from the first state to a third state upon exposure to the applied stimulant to conceal the unauthorized reprocessing warning;
wherein the unauthorized reprocessing warning is legible only after exposure to the applied stimulant and becomes concealed upon exposure to a reversion stimulant.

11. The medical device of claim 10, wherein the mask is disposed as fill about the unauthorized reprocessing warning.

12. The medical device of claim 10, wherein in the second state the first printable media is a first color, wherein in the third state the second printable media is a second color, wherein the first color and the second color are different with the second color concealing the first color.

13. The medical device of claim 10, wherein both the unauthorized reprocessing warning and the mask are configured to change state upon application of the reversion stimulant.

14. The medical device of claim 13, wherein the reversion stimulant comprises one of exposure to ultraviolet radiation or exposure to heat exceeding a predetermined threshold.

15. The medical device of claim 10, wherein the mask is configured to block out the unauthorized reprocessing warning upon exposure to the reversion stimulant.

16. A method of reprocessing a medical device, comprising:
receiving the medical device with an unauthorized reprocessing warning, printed in a first printable media configured to selectively change color, and a mask, printed in a second printable media configured to change color;
processing the medical device; and
exposing the medical device to a reversion stimulant, thereby transforming the unauthorized reprocessing warning to a state that is non-visible along the mask.

17. The method of claim 16, wherein exposing comprises one or more of exposing the medical device to ultraviolet radiation or exposing the medical device to heat exceeding a predetermined temperature threshold.

18. The method of claim 16, wherein the state comprises one of both the unauthorized reprocessing warning and the mask having a common color, or the mask concealing the unauthorized reprocessing warning.

19. The method of claim 16, wherein the state comprises both the unauthorized reprocessing warning and the mask being pellucid.

* * * * *